US007734007B2

(12) United States Patent
Kargar et al.

(10) Patent No.: US 7,734,007 B2
(45) Date of Patent: Jun. 8, 2010

(54) X-RAY IMAGING SYSTEM FOR PERFORMING AUTOMATED IMAGING OF PATIENT ANATOMY

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 10 days.

(21) Appl. No.: 12/366,292

(22) Filed: Feb. 5, 2009

(65) Prior Publication Data

US 2009/0238325 A1 Sep. 24, 2009

Related U.S. Application Data

(60) Provisional application No. 61/037,420, filed on Mar. 18, 2008, provisional application No. 61/037,424, filed on Mar. 18, 2008, provisional application No. 61/051,771, filed on May 9, 2008, provisional application No. 61/052,320, filed on May 12, 2008, provisional application No. 61/052,762, filed on May 13, 2008.

(51) Int. Cl.
  *A61B 6/00* (2006.01)
  *G01N 23/04* (2006.01)
  *H05G 1/02* (2006.01)

(52) U.S. Cl. .................. 378/8; 378/62; 378/196

(58) Field of Classification Search .............. 378/8, 378/19, 98.8, 147–153, 160, 205, 207, 196, 378/197
See application file for complete search history.

(56) References Cited

U.S. PATENT DOCUMENTS 4,744,099 A 5/1988 Huettenrauch et al.
(Continued)

*Primary Examiner*—Irakli Kiknadze
(74) *Attorney, Agent, or Firm*—Alexander J. Burke

(57) ABSTRACT

An X-ray imaging system performs automated imaging of patient anatomy. A collimator includes at least one portion of X-ray absorbent material automatically adjustable to alter the dimensions of a spatial cross section of an X-ray beam of radiation, in response to a control signal. A collimator controller generates the control signal in response to, determining one or more regions of the X-ray detector corresponding to a portion of patient anatomy to be X-rayed in response to X-ray absorbent markers indicating boundaries of the portion of patient anatomy during an initialization X-ray exposure for individual steps of the series of pre-programed steps and determining different positions of the portion of X-ray absorbent material for corresponding individual steps of a series of pre-programed steps in response to the determined regions. An X-ray imaging device automatically moves an X-ray detector and X-ray emitter combination relative to patient anatomy in a series of pre-programed steps, in response to data representing the determined series of pre-programed steps and user command. The X-ray imaging device automatically adjusts the position of the portion of X-ray absorbent material via the control signal.

19 Claims, 4 Drawing Sheets

U.S. PATENT DOCUMENTS

| | | |
|---|---|---|
| 5,917,882 A | 6/1999 | Khutoryansky et al. |
| 5,917,883 A | 6/1999 | Khutoryansky et al. |
| 6,501,828 B1 * | 12/2002 | Popescu ..................... 378/150 |
| 6,584,173 B2 | 6/2003 | Zwarf et al. |
| 6,980,623 B2 | 12/2005 | Dunhan et al. |
| 7,090,396 B2 * | 8/2006 | Boomgaarden ............. 378/196 |
| 7,340,033 B2 | 3/2008 | Mollus et al. |
| 7,344,305 B2 | 3/2008 | Kuzmanovic |
| 7,634,308 B2 * | 12/2009 | Ogawa ....................... 600/431 |
| 2002/0051516 A1 | 5/2002 | Zwarf et al. |
| 2006/0203966 A1 | 9/2006 | Mollus et al. |
| 2008/0025586 A1 | 1/2008 | Baumgart et al. |
| 2008/0037708 A1 | 2/2008 | Kuzmanovic |

* cited by examiner

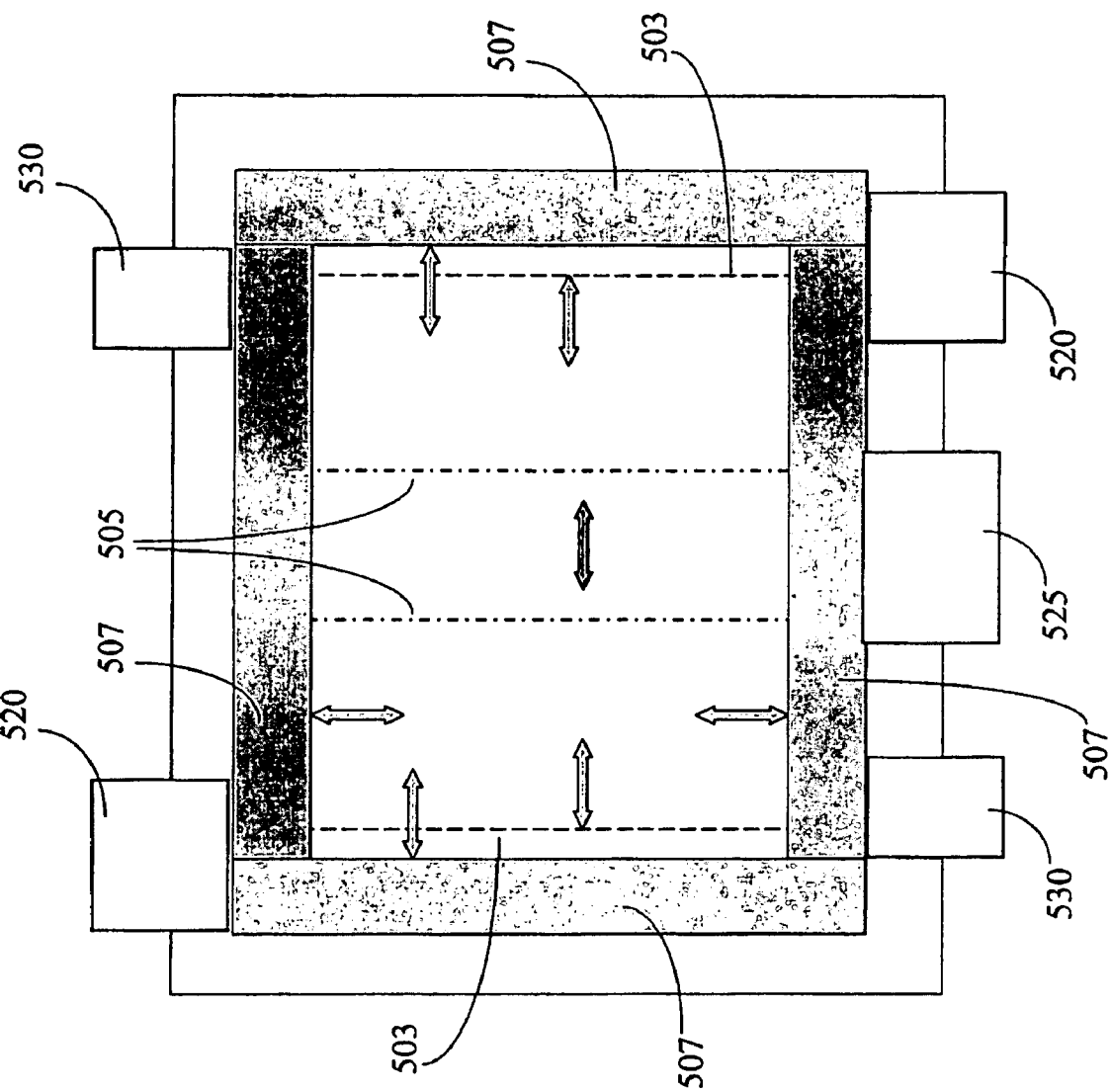

X-RAY IMAGING SYSTEM FOR PERFORMING AUTOMATED IMAGING OF PATIENT ANATOMY

This is a non-provisional application of provisional application Ser. No. 61/037,420 filed Mar. 18, 2008, provisional application Ser. No. 61/037,424 filed Mar. 18, 2008, provisional application Ser. No. 61/051,771 filed May 9, 2008, provisional application Ser. No. 61/052,320 filed May 12, 2008 and provisional application Ser. No. 61/052,762 filed May 13, 2008, by S. Kargar et al.

FIELD OF THE INVENTION

This invention concerns an X-ray imaging system for performing automated multi-step imaging of patient anatomy by automatically determining steps an X-ray device is to be moved and automatically adjusting a collimator, semi-transparent filters and an X-ray (finger) filter.

BACKGROUND OF THE INVENTION

In performing X-ray imaging angiography of the lower limbs of a patient, imaging usually starts at the pelvis and ends at the foot. The size of an imaging system X-ray radiation detector dictates image size. Thus, several images are acquired in a sequence of steps in order to cover an entire limb. The acquired images are joined (e.g., sewn) together and the entire limb image is created if so desired. Since each image is of a different part of the body, X-ray absorption differs in each X-ray imaging step. The X-ray radiation needs to be regulated and optimized for optimum image quality for individual steps.

In known systems, Peripheral Angiography workflow involves many user interactions. A user first performs X-ray imaging in individual steps (e.g., from the pelvis to the foot) on the patient lower limbs for configuration and to manually adjust a collimator, semi-transparent filters and finger filters for each step. A collimator narrows an X-Ray beam to cause the spatial cross section of the beam to become smaller and comprises individual plates or a diaphragm or system of diaphragms made of an absorbent material and arranged to determine the dimensions of an X-ray beam of radiation. Semi-transparent filters attenuate X-ray radiation provided from a radiation source to a portion of a patient and a finger filter attenuates substantially all X-ray radiation provided from a radiation source.

A user further performs X-ray imaging in individual steps on the patient lower limbs (from pelvis to foot) to determine a mask for subtraction of background detail. A third X-ray imaging pass is performed in individual steps on the patient lower limbs (from pelvis to foot), following injection of an X-ray contrast agent into the patient, to obtain desired X-ray images. In moving through the sequence of steps, the forward speed of movement of an X-ray source and detector combination relative to a patient table, is controlled by a user via a switch, for example. Known X-ray imaging of the limbs is cumbersome, involving multiple imaging passes and multiple steps as well as manual adjustment of a collimator, semi-transparent filters and finger filters for each individual step. A system according to invention principles automates a substantial portion of the process and addresses associated problems.

SUMMARY OF THE INVENTION

A system performs automated multi-step imaging of patient anatomy by automatically determining steps an X-ray device is to be moved and automatically adjusting a collimator, semi-transparent filters and an X-ray (finger) filter. An X-ray imaging system performs automated imaging of patient anatomy. A collimator includes at least one portion of X-ray absorbent material automatically adjustable to alter the dimensions of a spatial cross section of an X-ray beam of radiation, in response to a control signal. A collimator controller generates the control signal in response to, determining one or more regions of the X-ray detector corresponding to a portion of patient anatomy to be X-rayed in response to X-ray absorbent markers indicating boundaries of the portion of patient anatomy during an initialization X-ray exposure for individual steps of the series of pre-programmed steps and determining different positions of the portion of X-ray absorbent material for corresponding individual steps of a series of pre-programmed steps in response to the determined regions. An X-ray imaging device automatically moves an X-ray detector and X-ray emitter combination relative to patient anatomy in a series of pre-programmed steps, in response to data representing the determined series of pre-programmed steps and user command. The X-ray imaging device automatically adjusts the position of the portion of X-ray absorbent material via the control signal.

BRIEF DESCRIPTION OF THE DRAWING

FIG. 4 shows an adjustable collimator, semi-transparent filters and finger filter mounted in an X-ray radiation emitter unit, according to invention principles.

DETAILED DESCRIPTION OF THE INVENTION

Figure 1:
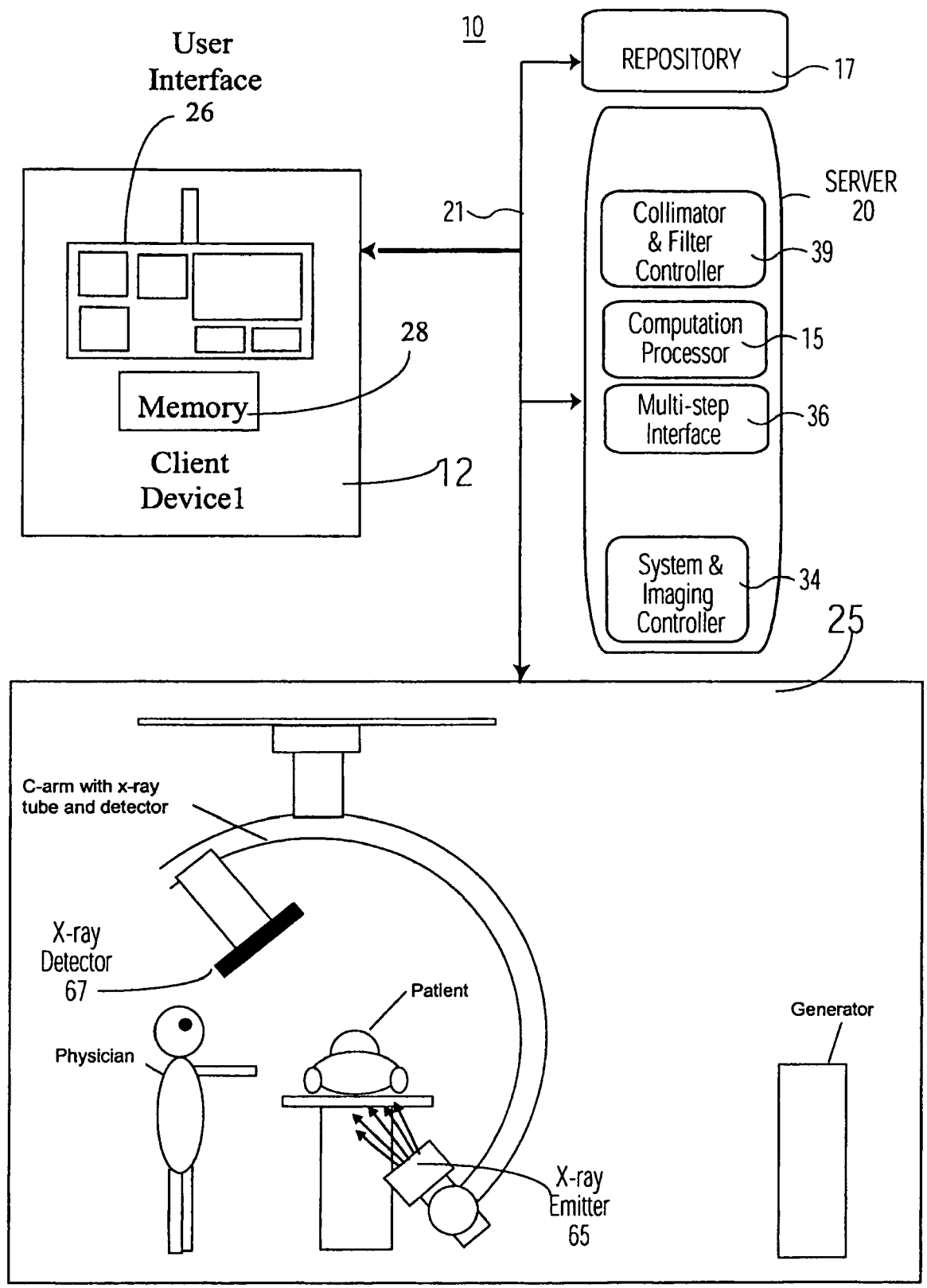
FIG. 1 shows an X-ray imaging system for performing automated multi-step imaging of patient anatomy, according to invention principles.

A system performs automated multi-step imaging of patient anatomy by automatically determining steps an X-ray device is to be moved and automatically adjusting a collimator, semi-transparent filters and an X-ray (finger) filter. The system streamlines Peripheral digital Angiography workflow, e.g., of patient limbs, by automatically calculating the number of steps needed for an X-ray imaging procedure and by automatically adjusting a collimator, semi-transparent filters and an X-ray finger filter. A user initiates performance of three X-ray imaging passes of one or more patient limbs, for example. These passes include a first fluoroscopy imaging pass for adjustment of collimator, Semi-transparent filters, finger filer and X-ray acquisition parameters, a second imaging pass for determining a mask image and a third imaging pass following injection of a contrast agent, to obtain digitally subtracted images of patient limbs, for example. Individual imaging passes involve multiple imaging steps through predetermined imaging positions to cover the full length of limbs. Further, in known systems in performing the first, second and third imaging passes, a user initiates movement of a radiation emitter and detector (e.g., mounted on a C-arm) relative to a patient table, to the predetermined imaging positions and manually adjusts a collimator, semi-transparent filters and finger filters (X-ray filters) for individual steps of at least one of the three imaging passes. The movement of the radiation emitter and detector on a C-arm, for example, or patient table may be controlled via joystick control. A system according to invention principles automates the repetitive steps to involve minimum user interaction.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

FIG. 1 shows X-ray imaging system 10 for performing automated multi-step imaging of patient anatomy. System 10 includes one or more processing devices (e.g., workstations, computers or portable devices such as notebooks, Personal Digital Assistants, phones) 12 that individually include memory 28 and a user interface 26 supporting image presentation in response to predetermined user (e.g., physician) specific preferences. System 10 also includes at least one repository 17, X-ray imaging modality system 25 and server 20 intercommunicating via network 21. User interface 26 provides data representing display images comprising a Graphical User Interface (GUI) for presentation on processing device 12. At least one repository 17 stores medical image studies for multiple patients in DICOM compatible (or other) data format. A medical image study individually includes multiple image series of a patient anatomical portion which in turn individually include multiple images. Server 20 includes, computation processor 15, collimator and filter controller 39, multi-step programming interface 36 and system and imaging controller 34. At least one repository 17 also includes predetermined data comprising, (a) a start position for X-ray imaging at a first location of a portion of patient anatomy and (b) an end position for X-ray imaging at a second location of a portion of patient anatomy. The predetermined data also comprises, (i) selected start and end positions for X-ray imaging the length of a portion of patient anatomy, (ii) the length of the portion of patient anatomy imaged in an individual step and (iii) overlap length desired between successive X-ray images.

X-ray imaging system 10 performs automated multi-step imaging for use in Peripheral Angiography of patient limbs such as legs, for example. X-ray imaging device 25 supports automated movement of an X-ray detector 67 and X-ray emitter 65 combination mounted on a C-arm, for example, relative to patient anatomy in a series of pre-programmed steps. X-ray emitter 65 includes a collimator, semi-transparent filters and an X-ray filter (finger filter) automatically adjustable to attenuate X-ray radiation in response to control signals. The collimator, semi-transparent filters and X-ray filter are located substantially close to an X-ray emitter source to attenuate X-ray radiation from X-ray emitter 65 before it passes through a patient. Multi-step programming interface 36 enables a user to select, (a) a start position for X-ray imaging at a first location of a portion of patient anatomy and (b) an end position for X-ray imaging at a second location of a portion of patient anatomy. The movable arm is movable to the start and end positions in response to user interaction and user interface 26 enables a user to select (and record data indicating) the start and end positions following movement of the arm and the X-ray detector 67 and X-ray emitter 65 combination relative to the portion of patient anatomy to the start and end positions respectively. X-ray imaging device 25 also includes a generator for providing power (such as high voltage power) for powering the X-ray emitter, for example.

Computation processor 15 (at least one computer) automatically determines a series of pre-programmed steps comprising multiple incremental distances to be moved by the X-ray detector 67 and X-ray emitter 65 combination relative to the portion of patient anatomy in response to, (i) the selected start and end positions, (ii) the length of the portion of patient anatomy imaged in an individual step, (iii) the amount of overlap desired between successive X-ray images and (iv) the area of the portion of patient anatomy imaged in an individual step. The length of the portion of patient anatomy imaged in an individual step is determined in response to an imaging zoom factor and the size of an imaging X-ray detector. Computation processor 15 automatically determines the multiple incremental distances by dividing a distance between the start and end positions by a distance moved by the X-ray detector 67 and X-ray emitter 65 combination relative to the portion of patient anatomy in an individual step. The distance moved by the X-ray detector 67 and X-ray emitter 65 combination relative to the portion of patient anatomy in an individual step is determined by subtracting a distance representing the overlap desired between successive X-ray images. Imaging controller 34 initiates automated multi-step imaging of the portion of patient anatomy by X-ray imaging device 25 in response to data representing the determined series of pre-programmed steps and user command.

X-ray emitter 65 includes a collimator, semi-transparent filters and an X-ray filter (finger filter). A collimator includes at least one portion of X-ray absorbent material automatically adjustable to alter the dimensions of a spatial cross section and determine a field of view of an X-ray beam of radiation, in response to a first control signal. Semi-transparent filters include at least one portion of X-ray filtering material automatically adjustable to attenuate X-ray radiation in response to a second control signal. The semi-transparent filters compensates for tissue density variation, specifically, for the difference in X-ray attenuation of different parts of patient anatomy (e.g., X-ray attenuation in the middle part of a leg containing bone is more than the sides). An X-ray (finger) filter is automatically adjustable to attenuate X-ray radiation to compensate for absence of tissue such as between legs, for example, in response to a third control signal.

Collimator and filter controller 39 generates the first, second and third control signals. Controller 39 generates the first and second control signals in response to, determining one or more regions of the X-ray detector corresponding to a portion of patient anatomy to be X-rayed in response to X-ray absorbent markers indicating boundaries of the portion of patient anatomy during an initialization X-ray exposure for individual steps of a series of pre-programmed imaging steps. Controller 39 generates the third control signal in response to, determining one or more second regions of the X-ray detector exposed to X-ray radiation un-attenuated by patient anatomy during an initialization X-ray exposure for individual steps of the series of pre-programmed steps. Controller 39 determines different first positions of the portion of X-ray absorbent material and different second positions of the X-ray filtering material for corresponding individual steps of the series of pre-programmed imaging steps in response to the determined regions. Controller 39 also determines different X-ray filter third positions for corresponding individual steps of the series of pre-programmed steps in response to the determined second regions. X-ray imaging device 25 automatically adjusts the position of the portion of X-ray absorbent material and the X-ray filtering material via the first and second control signals to the determined first and second positions respectively, for individual steps of the series of pre-programmed steps. Further, X-ray imaging device 25 automatically adjusts the X-ray filter position via the third control signal to the determined X-ray filter third positions to attenuate X-ray radiation un-attenuated by patient anatomy for individual steps of the series of pre-programmed steps, in response to the determined filter third positions.

Figure 2:
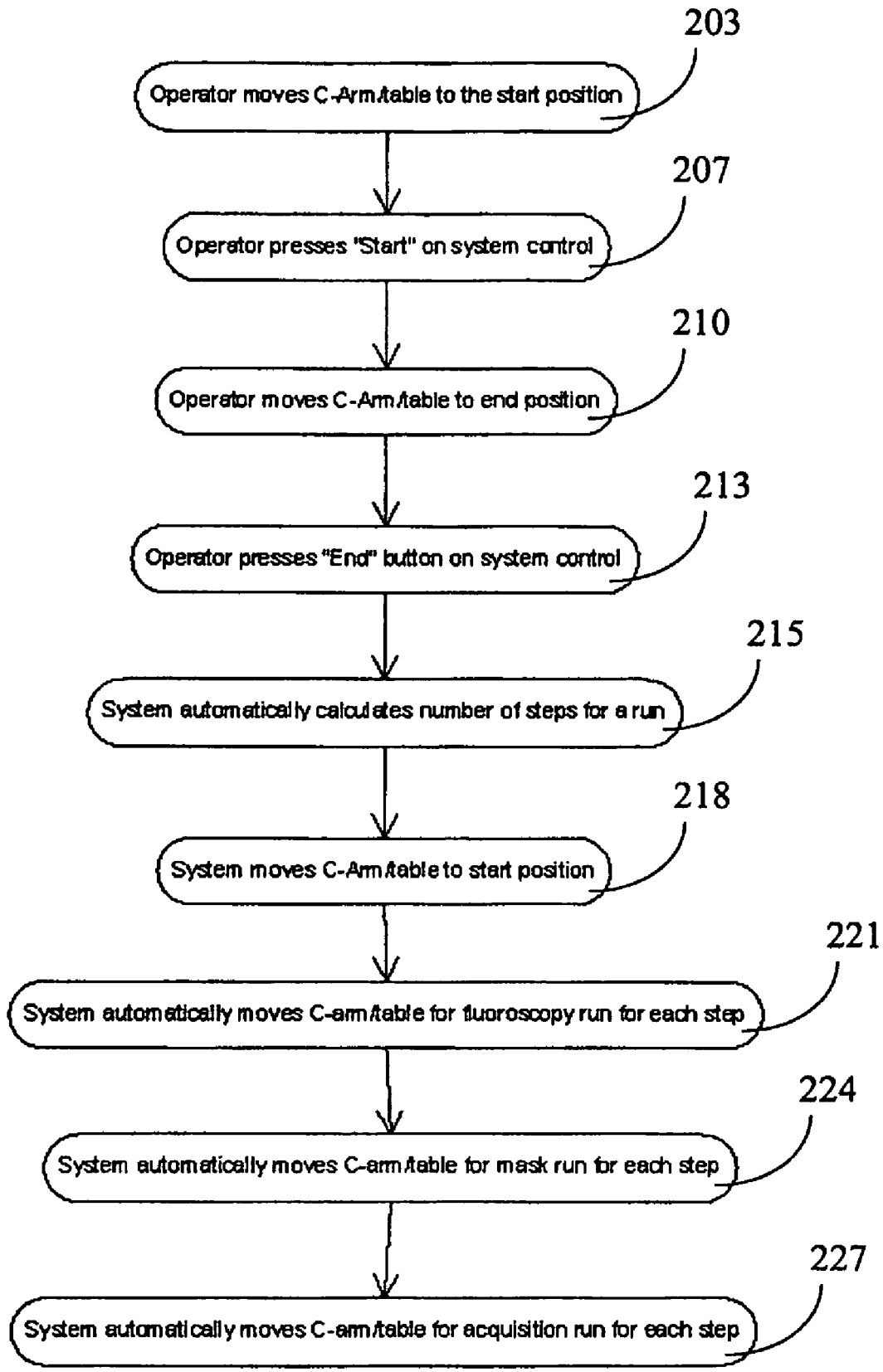
FIG. 2 shows a flowchart of a process performed by an X-ray imaging system for performing automated multi-step imaging of patient anatomy, according to invention principles.

FIG. 2 shows a flowchart of a process performed by X-ray imaging system 10 (FIG. 1) for performing automated multi-step imaging of patient anatomy. In step 203, a user employing multi-step programming interface 36 and controller 34, initiates automated movement of an X-ray detector 67 and X-ray emitter 65 combination mounted on a C-arm to a start position such as the pelvis when imaging lower limbs. In step 207 interface 36 records the start position arm location in response to user command. In step 210, a user employing multi-step programming interface 36 and controller 34, initiates automated movement of the X-ray detector 67 and X-ray emitter 65 combination to an end position such as the feet. In step 213 interface 36 records the end position arm location, in response to user command. In step 215, computation processor 15 automatically determines a series of pre-programmed steps comprising multiple incremental distances to be moved by the X-ray detector 67 and X-ray emitter 65 combination relative to the portion of patient anatomy from the selected start position to the end position. The determined distances are stored in at least one repository 17. Computation processor 15 automatically calculates the number of pre-programmed steps needed for use in each of three X-ray imaging passes (i.e., configuration, mask determination and imaging passes) and a user drives the C-arm or patient table to the start and end position.

Computation processor 15 processes the start and end position information and calculates the number of pre-programmed steps needed for the X-ray imaging pass. The number of steps is obtained by dividing the distance between the start and end positions by the selected zoom size. For instance, the distance between the pelvis and the foot of a patient is 72 cm and the zoom factor 2 i.e. 32 cm is selected. The numbers of steps are calculated by processor 15 as follows, Zoom factor 2 corresponds to a 22×22 cm area being covered by X-ray radiation detector 67. Overlap between each imaging step is 4 cm therefore, 22−4=18 cm is the distance traveled in each pre-programmed step by the X-ray detector 67 and X-ray emitter 65 combination relative to patient anatomy and 72/18=4 is the Number of pre-programmed steps needed to cover the limb.

In step 218 imaging controller 34 initiates movement of the X-ray detector 67 and X-ray emitter 65 combination on a C-arm, for example, to the start position and initiates a process of automatically moving the C-arm or a patient table for the individual pre-programmed steps for the three X-ray image acquisition passes (configuration, mask determination and imaging passes). In step 221, controller 34 automatically moves the C-arm or a patient table for the individual pre-programmed steps of a configuration (a fluoroscopy) imaging pass. A user initiates automatic adjustment of the X-ray filter, collimator and semi-transparent filters in individual pre-programmed steps of the configuration imaging pass. In step 224, controller 34 automatically moves the C-arm or a patient table for the individual pre-programmed steps of a mask determination imaging pass and in step 227, controller 34 automatically moves the C-arm or a patient table for the individual pre-programmed steps of an imaging pass, e.g., in the presence of a contrast agent to obtain digitally subtracted images of patient limbs.

Figure 3:
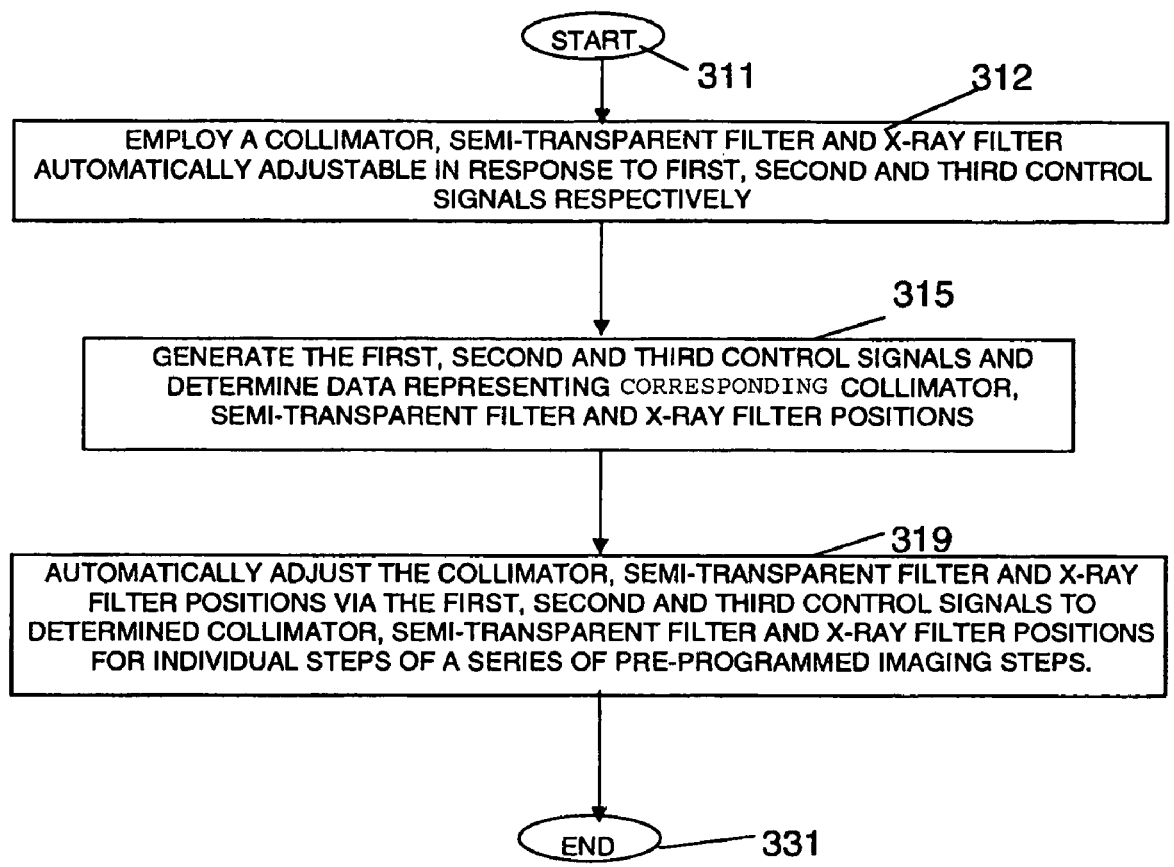
FIG. 3 shows a flowchart of a process performed by an X-ray imaging system for automatically adjusting an X-ray filter, collimator and semi-transparent filters, according to invention principles.

FIG. 3 shows a flowchart of a process performed by X-ray imaging system 10 (FIG. 1) for automatically adjusting an X-ray filter, collimator and semi-transparent filters. In step 312 following the start at step 311, imaging controller 34 initiates movement of the X-ray detector 67 and X-ray emitter 65 combination on a C-arm, for example, to a start position and initiates a process of automatically adjusting a collimator, semi-transparent filters and X-ray filter. A collimator in X-ray emitter 65 includes at least one portion of X-ray absorbent material automatically adjustable to alter the dimensions of a spatial cross section of an X-ray beam of radiation, in response to a first control signal. System 10 automatically adjusts plates of a collimator to improve image quality of lower limbs, for example, for angiography by detecting a position of a metal (e.g., lead (Pb)) or another X-ray attenuating object that is placed along the outer sides of patient legs. Semi-transparent filters in X-ray emitter 65 include at least one portion of at least partially X-ray absorbent material automatically adjustable to attenuate X-ray radiation in response to a second control signal. System 10 automatically adjusts the semi-transparent filters to improve image quality of lower limbs, for example, for angiography by detecting a position of a metal (e.g., lead (Pb)) or another X-ray attenuating object that is placed along the outer sides of patient legs. An X-ray filter (finger filter) in X-ray emitter 65 includes at least one portion of X-ray absorbent material automatically adjustable to attenuate X-ray radiation in response to a third control signal. System 10 automatically adjusts the X-ray filter to improve image quality of lower limbs, for example, for angiography by detecting an area of X-ray detector 67 receiving raw radiation (radiation un-attenuated by anatomical tissue).

In step 315, collimator and filter controller 39 generates the first, second and third control signals. Controller 39 generates the first and second control signals in response to, determining one or more regions of the X-ray detector corresponding to a portion of patient anatomy to be X-rayed in response to X-ray absorbent markers indicating boundaries of the portion of patient anatomy during an initialization X-ray exposure for individual steps of a series of pre-programmed imaging steps. Controller 39 generates the second control signal by determining one or more regions of the X-ray detector corresponding to a portion of patient anatomy to be X-rayed lying between X-ray absorbent markers and by determining regions of bone between X-ray absorbent markers. Collimator controller 39 determines the regions of bone between X-ray absorbent markers from one or more of, (a) X-ray imaging data and (b) estimation using at least one of, patient height, patient weight and a patient limb dimension. Controller 39 generates the third control signal in response to, determining one or more second regions of X-ray detector 67 exposed to X-ray radiation un-attenuated by patient anatomy during an initialization X-ray exposure for individual steps of the series of pre-programmed steps. Controller 39 determines different first positions of the portion of X-ray absorbent material and different second positions of the X-ray filtering material for corresponding individual steps of the series of pre-programmed imaging steps in response to the determined regions. Controller 39 also determines different X-ray filter third positions for corresponding individual steps of the series of pre-programmed steps in response to the determined second regions.

In step 319, X-ray imaging device 25 automatically adjusts the position of the portion of X-ray absorbent material and the X-ray filtering material via the first and second control signals to the determined first and second positions respectively, for individual steps of the series of pre-programmed steps. Further, X-ray imaging device 25 automatically adjusts the X-ray filter position via the third control signal to the determined X-ray filter third positions to attenuate X-ray radiation un-attenuated by patient anatomy for individual steps of the series of pre-programmed steps, in response to the determined filter third positions and user command. Further, X-ray imaging device 25 automatically moves the X-ray detector 67 and X-ray emitter 65 combination relative to patient anatomy in the series of pre-programmed steps during a configuration, mask determination and imaging pass (with contrast agent). System 10 automatically adjusts the X-ray filter, collimator and semi-transparent filters for individual steps of imaging passes using information determined during an initialization configuration (fluoroscopy) imaging pass. System 10 applies the determined information during a mask determination imaging pass and an imaging pass in the presence of a contrast agent. Specifically, after a mask determination imaging pass and injection of a contrast agent into a patient, a user initiates movement of a C-arm or patient table, for example by actuation of a switch so imaging follows the flow of the contrast agent.

Controller 39 may determine location of received raw radiation in the radiation detector 67 in different ways. In one embodiment, controller 39 derives a histogram representing image brightness of multiple individual pixels and identifies raw radiation in response to histogram luminance representative levels exceeding a predetermined threshold. Thereby a histogram is used to locate a distribution of raw radiation. An area with no dark pixels or few dark pixels, for example, as indicated by a pixel luminance threshold detector is identified as an area of raw radiation. In response to detection of a raw radiation area, controller 39 commands the X-ray filter to a desired position. Controller 39 automatically adjusts the X-ray filter position to the determined X-ray filter positions to attenuate X-ray radiation un-attenuated by patient anatomy for individual steps of the series of pre-programmed steps, in response to data representing the determined different positions. Another embodiment employs a closed feedback loop to move the X-ray filter and minimize an area of raw radiation detected by detector 67.

Controller 39 may determine location of X-ray absorbent markers indicating boundaries of the portion of patient anatomy in the radiation detector 67 in different ways. In one embodiment, in similar fashion to detection of raw radiation, controller 39 derives a histogram representing image brightness of multiple individual pixels and identifies an absorbent marker in response to histogram luminance representative levels below a predetermined threshold. Thereby a histogram is used to locate absorbent markers that indicate boundaries of a portion of patient anatomy such as a limb. An area with no light pixels or few light pixels, for example, as indicated by a pixel luminance threshold detector is identified as an absorbent marker. In response to detection of absorbent markers, controller 39 commands the adjustable collimator and adjustable semi-transparent filters to desired positions. Controller 39 automatically adjusts the adjustable collimator and adjustable semi-transparent filters positions to determined positions to attenuate X-ray radiation for individual steps of the series of pre-programmed steps, in response to data representing the determined different positions. In another embodiment a closed feedback loop is used to move the adjustable collimator and adjustable semi-transparent filters and maximize an area between absorbent markers identified by detector 67. In one embodiment, the adjustable collimator, adjustable semi-transparent filters and adjustable X-ray filter are adjusted in sequence. In another embodiment, they are adjusted in a different order. The process of FIG. 3 terminates at step 331.

FIG. 4 shows an adjustable unit comprising automatically adjustable collimator, semi-transparent filters and X-ray (finger filter) mounted in an X-ray radiation emitter 65 unit of X-ray imaging unit 25. The adjustable collimator comprises plates 507 automatically individually movable by actuators 520 (e.g., stepper motors) to expand or reduce X-ray beam cross-section and determine an X-ray field of view, in response to a control signal provided by controller 39 (FIG. 1). The adjustable semi-transparent filters comprises semi-transparent filters 503 automatically individually movable by actuators 530 (e.g., stepper motors) to expand or reduce a portion of the X-ray beam that is attenuated in response to a control signal provided by controller 39. The semi-transparent filters is adjusted to compensate for tissue density variation resulting in difference in X-ray attenuation of different parts of anatomy such as a leg (X-ray attenuation of the middle part of a leg including bone is typically greater than the sides of the leg).

The X-ray attenuation characteristics of the X-ray absorbent markers placed along sides of the legs, for example, are different from body tissue enabling the system to detect where the markers are during an initialization configuration (fluoroscopy) imaging pass. Controller 39 adjusts the collimator plates and semi-transparent filters to detected position of the markers or positions relative to the markers. System 10 thereby automatically regulates X-ray radiation to optimize image quality of the lower limbs for each step of the different imaging passes. The adjustable X-ray filter comprises plates 505 automatically individually movable by actuator 525 (e.g., a stepper motor) to expand or reduce a portion of the X-ray beam that is attenuated in response to a control signal provided by controller 39 derived in response to detection by the X-ray detector 67 of an area of raw radiation. Controller 39 moves the X-ray filter to attenuate radiation that passes between patient legs, for example, to compensate for absence of tissue. In other embodiments, the adjustable collimator, semi-transparent filters and X-ray filter may comprise different adjustable plates and attenuation materials involving different geometries, shapes, sizes and angles.

The systems and processes of FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system provides automatic calculation of the number of steps involved in peripheral angiography and imaging of body parts or objects that require multiple frames to be sewn together to get a complete picture of the object. The system provides automatic positioning of an adjustable collimator, semi-transparent filters and X-ray filter and may be used in any diagnostic or interventional X-ray system. Further, the processes and applications may, in alternative embodiments, be located on one or more (e.g., distributed) processing devices. Any of the functions and steps provided in FIGS. 1-4 may be implemented in hardware, software or a combination of both.

What is claimed is:

1. An X-ray imaging system for performing automated imaging of patient anatomy, comprising:
   at least one repository of data determining a series of pre-programmed steps comprising a plurality of incremental distances to be moved by an X-ray detector and X-ray emitter combination relative to a portion of patient anatomy;
   a collimator including at least one portion of X-ray absorbent material automatically adjustable to alter the dimensions of a spatial cross section of an X-ray beam of radiation, in response to a control signal;
   a collimator controller for generating said control signal in response to,
      determining one or more regions of the X-ray detector corresponding to a portion of patient anatomy to be X-rayed in response to X-ray absorbent markers indicating boundaries of said portion of patient anatomy during an initialization X-ray exposure for individual steps of said series of pre-programmed steps and
      determining different positions of said portion of X-ray absorbent material for corresponding individual steps of said series of pre-programmed steps in response to the determined regions; and
   an X-ray imaging device for automatically moving an X-ray detector and X-ray emitter combination relative to patient anatomy in a series of pre-programmed steps, in response to data representing the determined series of pre-programmed steps and user command and automatically adjusting the position of said portion of X-ray absorbent material via said control signal to the determined positions of said portion of X-ray absorbent material to limit the spatial cross section of an X-ray beam of radiation for individual steps of said series of pre-programmed steps.

2. A system according to claim 1, wherein said X-ray absorbent markers are metallic lead (Pb) markers.

3. A system according to claim 2, wherein said collimator controller generates said control signal by determining one or more regions of the X-ray detector corresponding to a portion of patient anatomy to be X-rayed lying between X-ray absorbent markers.

4. A system according to claim 1, wherein said X-ray imaging device automatically moves said X-ray detector and X-ray emitter combination relative to patient anatomy in said series of pre-programmed steps during a mask determination X-ray exposure.

5. A system according to claim 1, wherein said X-ray imaging device automatically moves said X-ray detector and X-ray emitter combination relative to patient anatomy in said series of pre-programmed steps during an X-ray imaging exposure in the presence of a contrast agent.

6. An X-ray imaging system for performing automated imaging of patient anatomy, comprising:
   at least one repository of data determining a series of pre-programmed steps comprising a plurality of incremental distances to be moved by an X-ray detector and X-ray emitter combination relative to a portion of patient anatomy;
   a semi-transparent filter including at least one portion of X-ray filtering material automatically adjustable to attenuate X-ray radiation in response to a control signal;
   a filter controller for generating said control signal in response to,
      determining one or more regions of the X-ray detector corresponding to a portion of patient anatomy to be X-rayed in response to X-ray absorbent markers indicating boundaries of said portion of patient anatomy during an initialization X-ray exposure for individual steps of said series of pre-programmed steps and
      determining different positions of said X-ray filtering material for corresponding individual steps of said series of pre-programmed steps in response to the determined regions; and
   an X-ray imaging device for automatically moving an X-ray detector and X-ray emitter combination relative to patient anatomy in a series of pre-programmed steps, in response to data representing the determined series of pre-programmed steps and user command and automatically adjusting the position of said X-ray filtering material via said control signal to the determined positions of said X-ray filtering material to attenuate an X-ray beam of radiation in part of said portion of patient anatomy for individual steps of said series of pre-programmed steps.

7. A system according to claim 6, wherein said X-ray absorbent markers are metallic lead (Pb) markers.

8. A system according to claim 6, wherein
said X-ray imaging device automatically moves said X-ray detector and X-ray emitter combination relative to patient anatomy in said series of pre-programmed steps during a mask determination X-ray exposure.

9. A system according to claim 8, wherein
said X-ray imaging device automatically moves said X-ray detector and X-ray emitter combination relative to patient anatomy in said series of pre-programmed steps during an X-ray imaging exposure in the presence of a contrast agent.

10. A system according to claim 6, wherein
said collimator controller generates said control signal by determining one or more regions of the X-ray detector corresponding to a portion of patient anatomy to be X-rayed lying between X-ray absorbent markers.

11. A system according to claim 10, wherein
said collimator controller generates said control signal by determining one or more regions of the X-ray detector corresponding to a portion of patient anatomy to be X-rayed lying between X-ray absorbent markers and by determining regions of bone between X-ray absorbent markers.

12. A system according to claim 10, wherein
said collimator controller determines said regions of bone between X-ray absorbent markers from X-ray imaging data.

13. A system according to claim 10, wherein
said collimator controller determines said regions of bone between X-ray absorbent markers from estimation using at least one of, (a) patient height, (b) patient weight and (c) a patient limb dimension.

14. An X-ray imaging system for performing automated imaging of patient anatomy, comprising:
a collimator including at least one portion of X-ray absorbent material automatically adjustable to alter the dimensions of a spatial cross section of an X-ray beam of radiation, in response to a first control signal;
a semi-transparent filters including at least one portion of X-ray filtering material automatically adjustable to attenuate X-ray radiation in response to a second control signal;
a controller for generating the first and second control signals in response to,
  determining one or more regions of the X-ray detector corresponding to a portion of patient anatomy to be X-rayed in response to X-ray absorbent markers indicating boundaries of said portion of patient anatomy during an initialization X-ray exposure for individual steps of a series of pre-programmed imaging steps and
  determining different first positions of said portion of X-ray absorbent material and different second positions of said X-ray filtering material for corresponding individual steps of said series of pre-programmed imaging steps in response to the determined regions; and
an X-ray imaging device for automatically adjusting the position of said portion of X-ray absorbent material and said X-ray filtering material via said first and second control signals to the determined first and second positions respectively, for individual steps of said series of pre-programmed steps.

15. A system according to claim 14, including
at least one repository of data determining said series of pre-programmed imaging steps comprising a plurality of incremental distances to be moved by an X-ray detector and X-ray emitter combination relative to said portion of patient anatomy.

16. A system according to claim 14, wherein
said X-ray imaging device automatically moves an X-ray detector and X-ray emitter combination relative to patient anatomy in said series of pre-programmed imaging steps, in response to data representing the determined series of pre-programmed imaging steps and user command.

17. A system according to claim 14, including
an X-ray filter automatically adjustable to attenuate X-ray radiation in response to a third control signal and
said controller generates said third control signal in response to,
  determining one or more second regions of the X-ray detector exposed to X-ray radiation un-attenuated by patient anatomy during an initialization X-ray exposure for individual steps of said series of pre-programmed steps and
  determining different X-ray filter third positions for corresponding individual steps of said series of pre-programmed steps in response to the determined second regions.

18. A system according to claim 17, wherein
said X-ray imaging device automatically adjusts the X-ray filter position via said third control signal to the determined X-ray filter third positions to attenuate X-ray radiation un-attenuated by patient anatomy for individual steps of said series of pre-programmed steps, in response to the determined filter third positions.

19. A system according to claim 14, including
a computation processor for automatically determining said series of pre-programmed steps comprising a plurality of incremental distances to be moved by an X-ray detector and X-ray emitter combination relative to said portion of patient anatomy in response to,
  (i) the selected start and end positions,
  (ii) the length of said portion of patient anatomy imaged in an individual step and
  (iii) the amount of overlap desired between successive X-ray images.

* * * * *